United States Patent [19]

Schmid

[11] 4,363,245

[45] Dec. 14, 1982

[54] SAMPLING APPARATUS

[75] Inventor: Carl J. Schmid, Port Washington, N.Y.

[73] Assignee: Peerless Electronics Research Corp., Westbury, N.Y.

[21] Appl. No.: 207,908

[22] Filed: Nov. 18, 1980

[51] Int. Cl.³ .............................................. G01N 1/00
[52] U.S. Cl. ................................. 73/864.22; 198/724; 198/778; 422/65
[58] Field of Search ...................... 141/1, 98, 130, 89, 141/90, 91, 92; 73/863.91, 863.92, 864.82, 864.22; 198/724, 778, 339; 422/65; 134/22.12

[56] References Cited
U.S. PATENT DOCUMENTS

| 3,134,263 | 5/1964 | De Jong . | |
| 3,230,776 | 1/1966 | Isreeli et al. . | |
| 3,836,329 | 9/1974 | Jordan | 134/22.12 |
| 3,881,872 | 5/1975 | Naono | 134/22.12 |

*Primary Examiner*—Houston S. Bell, Jr.
*Attorney, Agent, or Firm*—Lee C. Robinson, Jr.

[57] ABSTRACT

A liquid sampling apparatus includes a sample carrier supporting a plurality of sample containers arrayed in a generally spiral pattern for successive passage through a sampling station at which a sampling tube removes a small quantity of liquid from each container. A receptacle for containing a wash liquid is located adjacent the sampling station, and the wash liquid is supplied to the sampling tube between the taking of successive samples in order to cleanse the sampling tube.

14 Claims, 10 Drawing Figures

SAMPLING APPARATUS

The present invention relates to automatic liquid sampling apparatus and more particularly to a sampling device in which successive liquid samples can be obtained and transmitted to a liquid analysis device.

Automatic liquid sampling apparatus is particularly adapted for use in the medical profession to take successive samples of blood, blood serum, or similar body fluids, and supply them to an automatic liquid analysis apparatus for quantitative analysis. In such liquid sampling apparatus, the successive samples must be segregated from one another and the sampling device must be cleansed between the taking of successive samples so that the samples are not contaminated by each other.

An object of the present invention is to provide an improved liquid sampling apparatus which contains provision for supplying a wash liquid to the sampling tube of the device between the taking of successive samples.

Another object of the present invention is to provide an improved liquid sampling apparatus which has a stationary sampling station to which successive liquid samples are supplied.

A still further object of the present invention is to supply a liquid sampling apparatus which has the capacity of presenting a large number of liquid samples to a single sampling station within a confined space.

Yet another object of the present invention is to provide a liquid sampling apparatus which is relatively simple in construction and durable in use.

A still further object of the present invention is to provide an improved liquid sampling apparatus which has an accurate indexing arrangement for successively presenting a plurality of liquid sample containers at a fixed sampling station.

In accordance with an aspect of the present invention, a liquid sampling apparatus is provided which includes a support arm pivotally mounted in a housing for the apparatus. The support arm carries a sample carrier disk rotatably mounted thereon. The disk includes a plurality of sample container openings formed therein, arrayed in a generally spiral pattern about the pivotal mounting of the disk, in which sample containers are supported. These spirally arrayed sample containers are successively moved into and through a fixed sampling station upon coordinated rotation of the disk and pivoting of the arm to successively position each of the sampling containers at the fixed sampling station.

A receptacle containing a wash liquid is located adjacent to the sampling station and a tubular member or needle is provided to selectively remove a sample of liquid from a sample container at the sampling station. After a sample is taken, the tube is moved vertically with respect to the sample container at the sampling station and then horizontally, to a position over the wash liquid receptacle. At that point, the receptacle, being vertically movably mounted, moves upwardly to immerse the sampling tube in the wash liquid.

The above, and other objects, features and advantages of this invention, will be apparent in the following detailed description of an illustrative embodiment thereof which is to be read in connection with the accompanying drawings, wherein.

Figure 1:
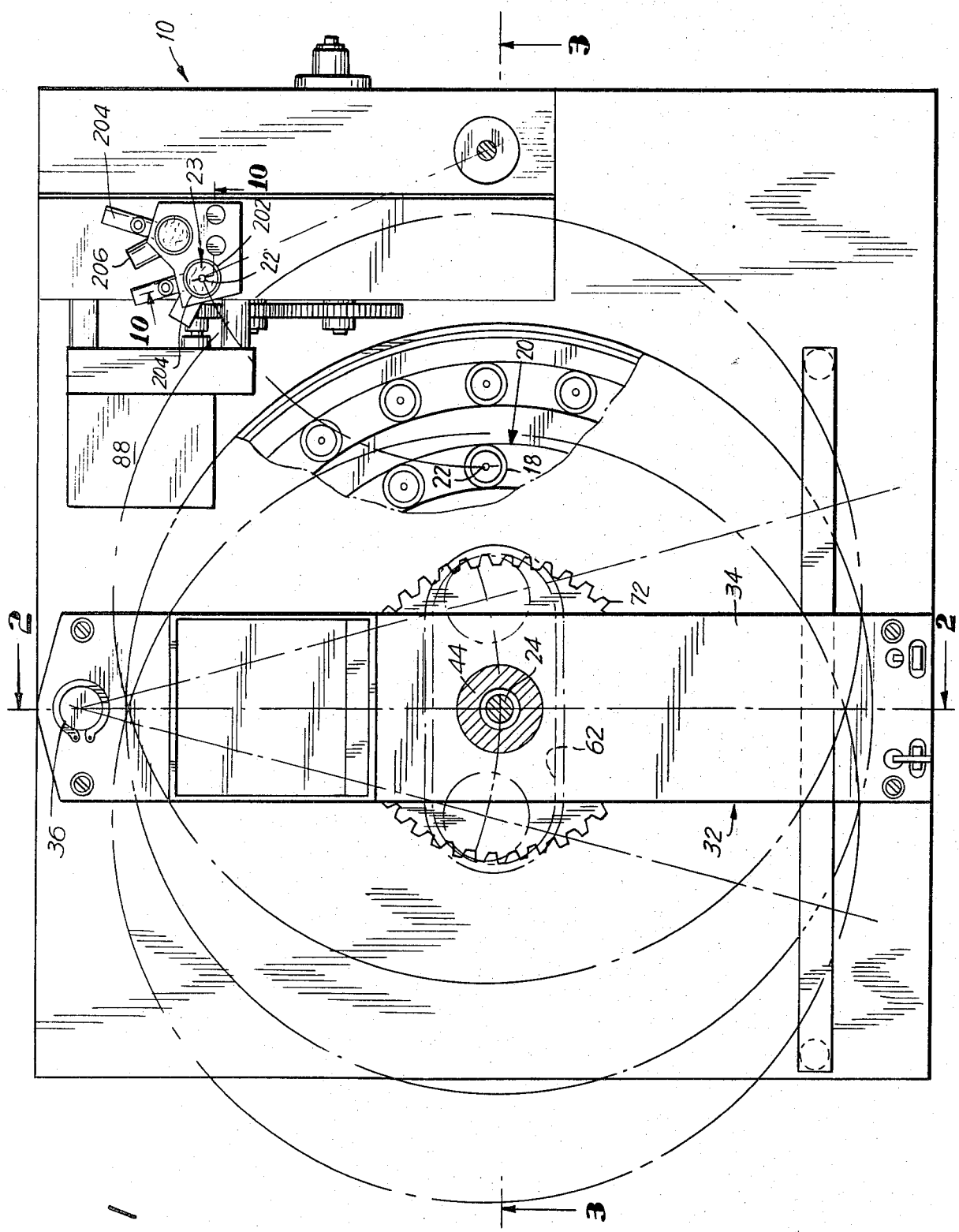
FIG. 1 is a sectional view, in plan, through the liquid sampling apparatus of the present invention, taken along line 1—1 of FIG. 2.
Figure 2:
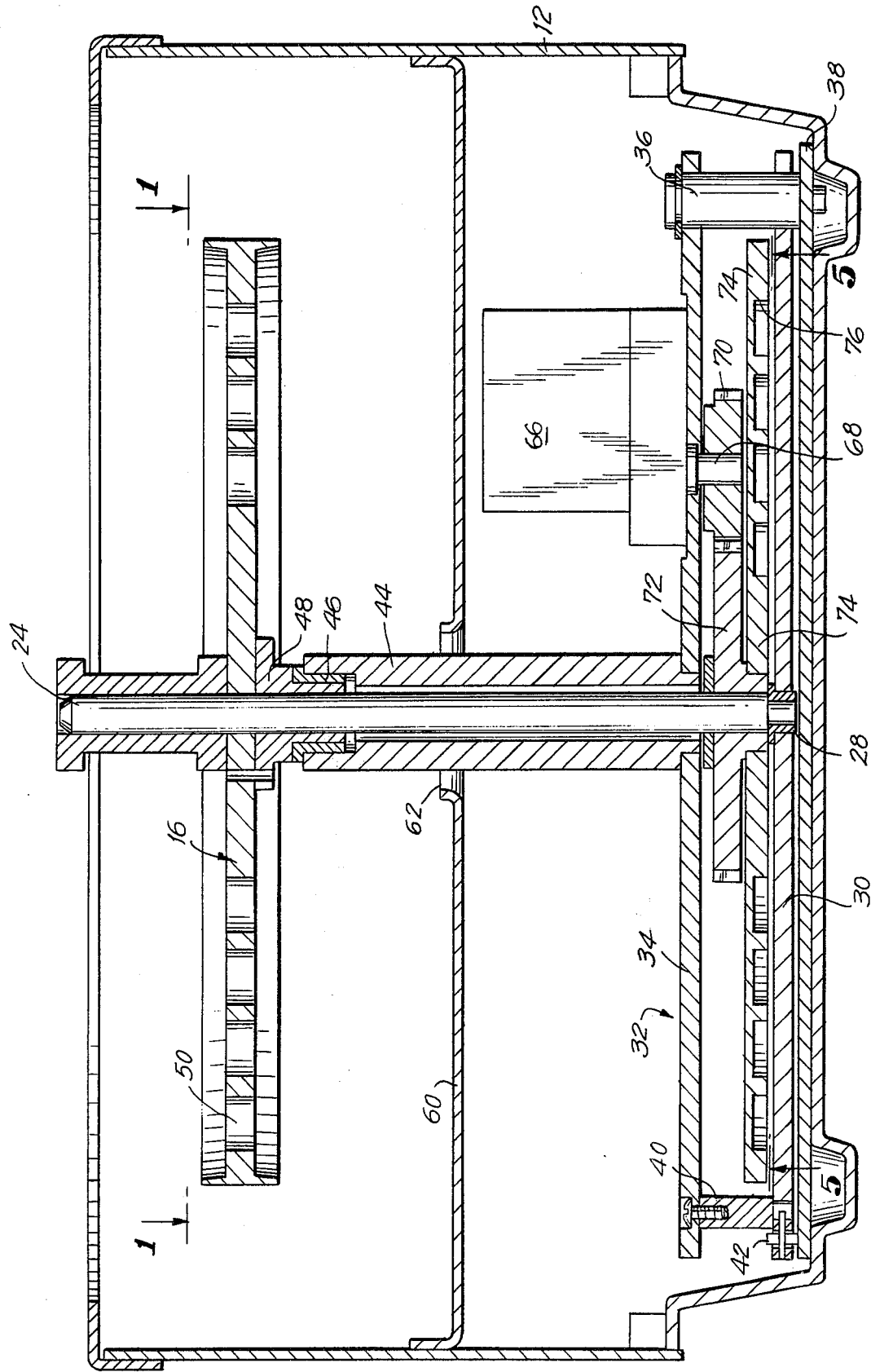
FIG. 2 is a vertical sectional view of the apparatus taken along line 2—2 of FIG. 1.
Figure 3:
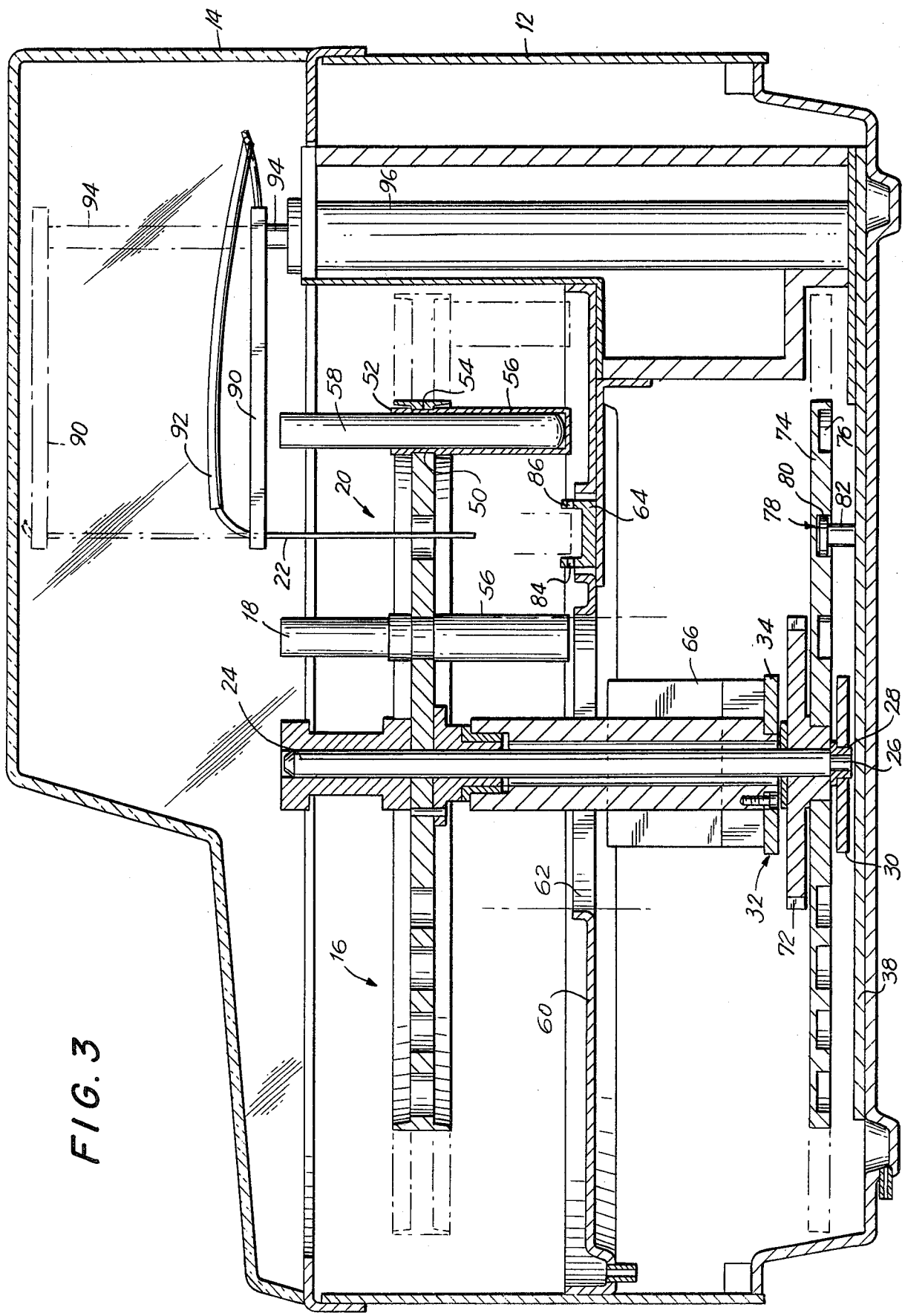
FIG. 3 is a vertical sectional view taken along line 3—3 of FIG. 1.
Figure 5:
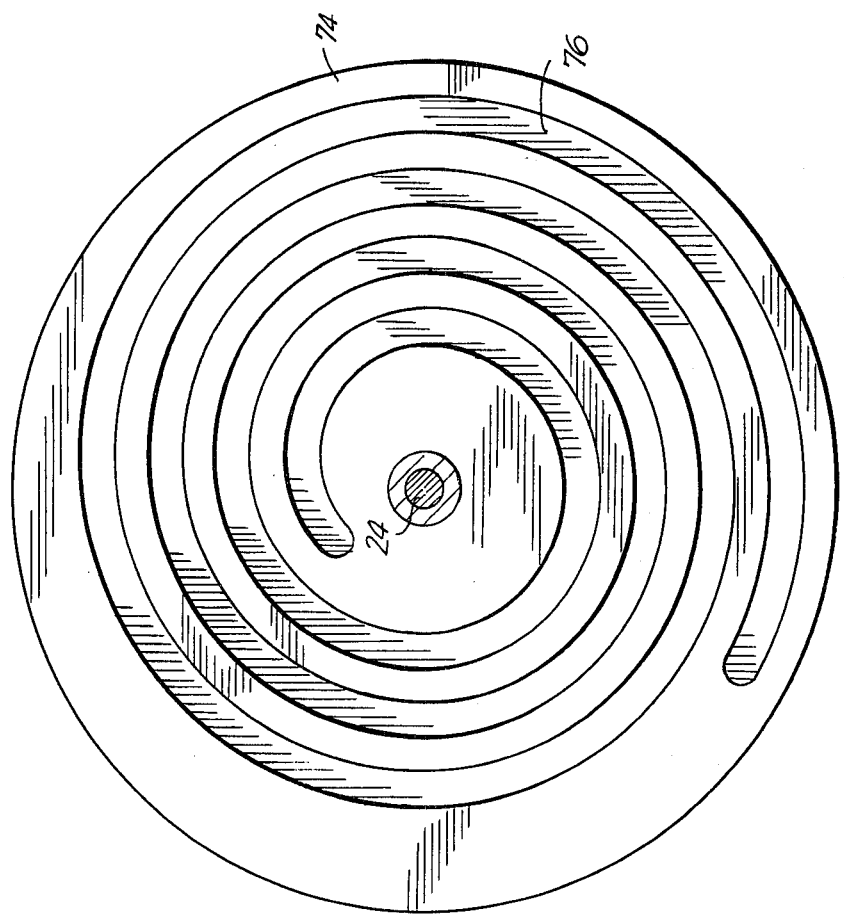
FIG. 5 is a bottom plan view of the cam disk used in the apparatus of the present invention.

Referring now to the drawings in detail and initially to FIGS. 1, 2 and 3 thereof, a liquid sampling apparatus 10, constructed in accordance with the present invention, includes a casing or frame 12 on which a removable, transparent cover 14 is mounted. The casing contains a sample carrier disk 16 which is rotatably mounted in the casing and driven to successively present sample containers 18 supported therein at a sampling station 20. A sampling tube 22 is located within the apparatus at station 20. The tube is mounted for vertical movement, as shown in dotted lines in FIG. 3, and for horizontal swinging movement, as shown in dotted lines in FIG. 1.

When a sample container 18 arrives at sampling station 20, sampling tube 22 is moved downwardly into the container and a sample of liquid therein is aspirated through the tube which is connected to a peristaltic pump, for example of the type disclosed in U.S. Pat. No. 4,233,001, granted Nov. 28, 1979, the disclosure of which is incorporated herein by reference. Thereafter, the tube is raised to the phantom line position in FIG. 3 as the sample passes through the pump to a suitable liquid analysis apparatus, for example of the type shown in U.S. Pat. No. 4,273,449 granted June 16, 1981, the disclosure of which is incorporated herein by reference. When the tube reaches its raised phantom line position, it is swung through an arc of about 66°, as illustrated in FIG. 1, to a position over a wash liquid receptacle 23, mounted in the apparatus adjacent the sampling station. When the sampling tube arrives at this position, the wash liquid receptacle is raised in order to immerse the tube in the wash liquid. This cleanses the tube and causes aspiration of a small amount of the wash liquid into the tube, so that the interior thereof is also cleansed. As a result, contamination of the next sample to be taken is avoided. In a timed, programmed sequence of operations, wash liquid receptacle 23 then moves downwardly, away from sampling tube 22, which is thereafter returned to the sampling station over carrier 16, where it remains until the next sample container 18 arrives at the sampling station.

Sampling disk 16 is a generally circular member which is fixed or keyed to a central shaft 24 in the apparatus. Shaft 24 extends vertically, and has its lower end 26 received in a sleeve bearing 28 that is rotatably mounted in the bottom arm 30 of an arm support assembly 32. The latter includes the lower arm 30 and an upper arm 34. These two arms are pivotally mounted on a pivot post 36, secured to a bottom support plate 38 in the apparatus. The ends of arms 30, 34, opposite pivot post 36, are rigidly secured together by a connecting block 40, with lower arm 30 having roller bearings 42 rotatably mounted therein. These roller bearings rest on plate 38 and support the end of the arm during its oscillating movement, between the phantom line positions thereof shown in FIG. 1, as described hereinafter.

A support sleeve 44 is secured to the upper arm 34 of arm assembly 32 and has a sleeve bearing 46 mounted therein at its upper end. The hub 48 of disk 16 is received within sleeve bearing 46 so that the disk and shaft 24 can rotate with respect to sleeve 44.

Figure 4:
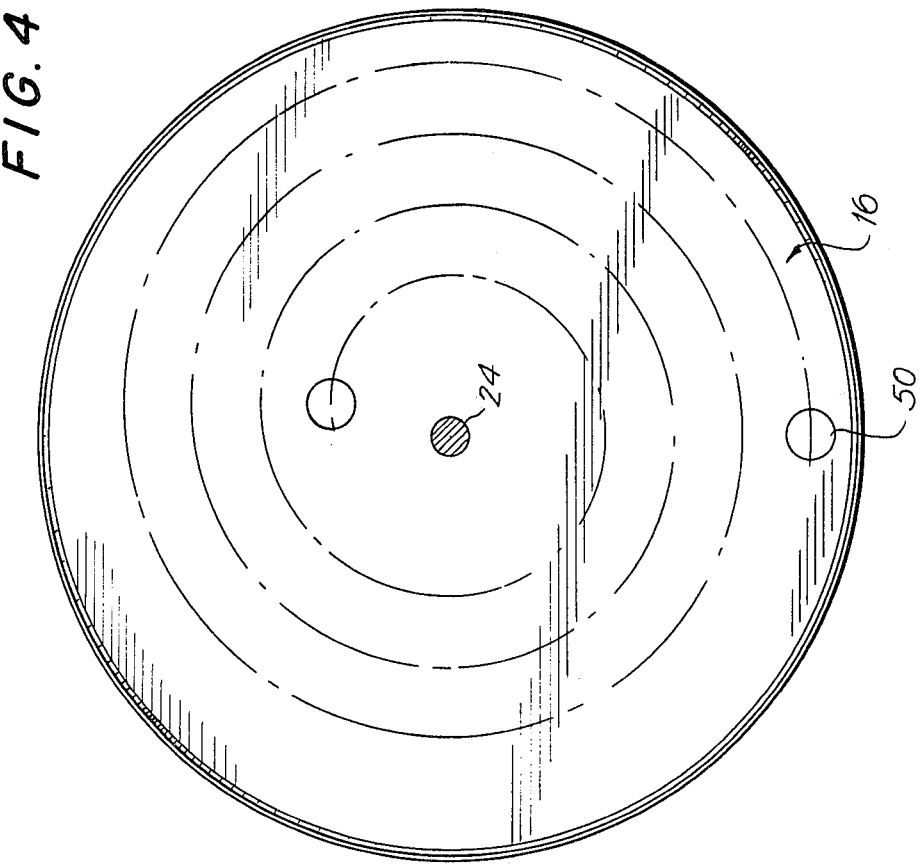
FIG. 4 is a bottom plan view of the sample container carrier disk used in the apparatus of the present invention.

Disk 16 has a plurality (one hundred and one, in the illustrated embodiment) of openings 50 formed therein. These openings are arrayed in a generally spiral pattern about central support shaft 24, as seen in FIG. 4. The openings provide support for carrier elements 52, which can be frictionally engaged in openings 50. As seen in FIG. 2, carrier support 52 is an opaque element having an annular groove 54 formed therein that snap-fits in openings 50. A separate carrier may be provided in each of the openings 50, although only sufficient carriers to accomodate the samples being taken are actually required during use of the apparatus.

Carriers 52 are generally hollow members and their generally cylindrical interiors 56 accommodate sample test tubes or containers 58.

A central plate 60 is provided in the liquid sampling apparatus to separate the upper sample carrier disk from the lower arm assembly 34 and the drive and transmission mechanisms for the device, thereby to aid in insuring sterile conditions in the area of the sample. Separating plate 60 has an elongated slot 62 formed therein which permits shaft 24 and sleeve 44 to oscillate between the phantom line positions shown in FIG. 1. In addition, separator plate 60 carries a sensing device 64 at the sampling station 20, which device determines the presence of a sample at the sampling station and initiates actuation of movement of the sampling tube 22 and the wash liquid receptacle, as described hereinafter.

Each of the successive sample openings 50 is presented at sampling station 20 as a result of the novel drive arrangement for the apparatus provided in accordance with the present invention. This drive arrangement includes a drive motor 66 mounted on upper arm 34 of arm assembly 32. The drive motor includes an output shaft 68 (FIG. 2) to which a gear 70 is secured. The latter meshes with and drives a larger gear 72 that is secured to shaft 24 in order to rotate the shaft and thus disk 16.

Because of the spiral array of the sample container support openings 50, it is necessary to advance the carrier disk in a horizontal direction, as well as in an angular direction, in order to move successive openings 50 to the fixed sampling station 20. This is accomplished by the provision of a cam disk 74 which is keyed or otherwise fixed to gear 72 for rotation with it, shaft 24 and disk 16. Cam disk 74 has a generally spirally shaped downwardly opening slot 76 formed therein which is generally complementary to the spiral array of openings 50.

A cam follower 78 (FIG. 3) is engaged in slot 76 and includes an upper roller 80 rotatably mounted on a post 82 secured to bottom plate 38. Because of the engagement of the cam roller in slot 76 rotation of cam disk 74 will cause the disk to move laterally as the slot moves over the roller. This will cause arm assembly 32 to swing between the extremes thereof illustrated in phantom lines in FIG. 1. Because the configuration of slot 76 is complementary to the array of openings 50 in disk 16, as disk 16 rotates to present the next opening 50 at station 20, the arm assembly 32 will also move slightly horizontally, thereby also moving the carrier disk slightly horizontally, in order to insure that the next opening 50 aligns properly with sampling station 20.

Figure 6:
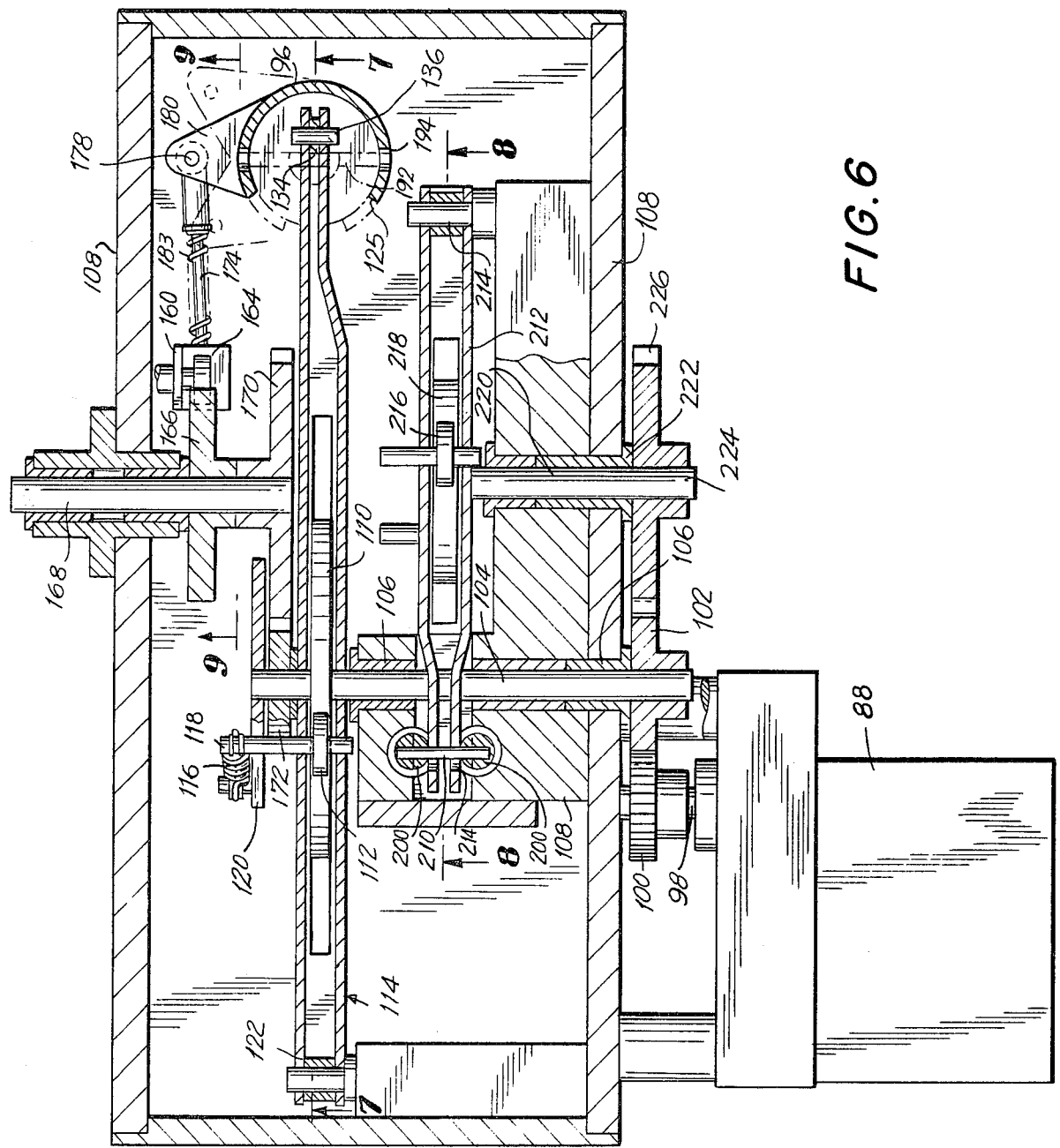
FIG. 6 is a top plan view, partly in section, of the drive transmission used to oscillate the sampling tube between the sampling station and the wash liquid receptacle.

When a sampling container arrives at sampling station 20, the lower end of the container support passes through sensor element 64. That sensor includes a light emitting diode 84 mounted on one side thereof and a photo-transistor 86 mounted at the other. The presence of the container between the light emitting diode and the photo-transistor opens the circuit therebetween and causes current to the motor 66 to be shut off so that the apparatus stops with the sampling container at station 20. Simultaneously, deactivation of the circuit formed by the light emitting diode and the photo-transistor causes actuation of a second drive motor 88 (see FIG. 6) which controls the movement of sampling tube 22.

It will be understood that the specific electronic control circuits for the motors 66, 88, and the light emitting diodes 84 and 86, are not described herein in detail, as such circuits are conventional control circuits, which can be readily constructed by those skilled in the electronics art.

Sampling tube 22 is formed of a rigid, hollow material, such as plastic or metal, and is mounted on a arm 90. A flexible tube 92 extends along arm 90 and is in communication with the upper end of tube 22. Tube 90 is connected to an aspirator or vacuum device, in the conventional manner, to draw a sample of liquid from the container and move it to a liquid analysis apparatus.

Normally, sampling tube 22 is located in the phantom line position shown in FIG. 3, i.e. in its upper position. It is held in this upper position by the support rod 94 on which rod 90 is rigidly mounted. Rod 94 is vertically slidably mounted in a tube 96 in order to move the sampling tube from its upper position to its lower position, shown in solid lines in FIG. 3, wherein it is located within a sampling container, so that the liquid in the container can be aspirated.

As mentioned, vertical movement of sampling tube 22 is under the control of motor 88. That motor includes an output shaft 98 to which a spur gear 100 is drivingly engaged. That gear, in turn, meshes with a second spur gear 102 secured to a subshaft 104 rotatably mounted by sleeve bearings 106 in a subhousing 108 of the apparatus.

A first cam 110 is fixed to shaft 104 and is located in engagement with a cam follower 112. The latter is rotatably mounted on a pivot arm 114 (see FIG. 7) and is biased into engagement with cam 110 by a spring 116 connected between the cam follower's shaft 118 and a support plate 120 of subhousing 108.

Figure 7:
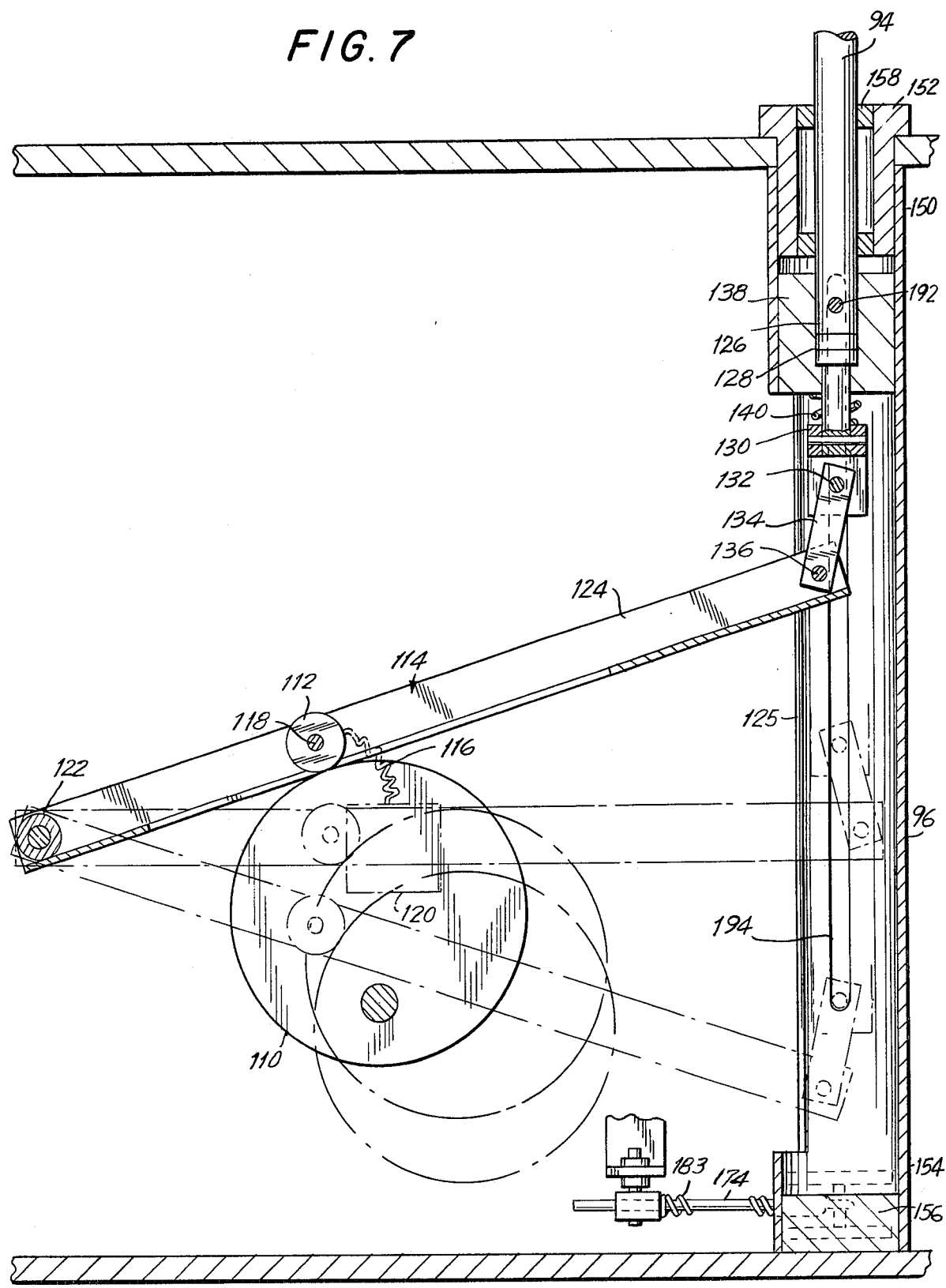
FIG. 7 is a sectional view of the device for raising and lowering the sampling tube, taken along line 7—7 of FIG. 6.

Lever 114 is pivotally mounted at one end 122 in subhousing 108 and its opposite end 124 extends through a vertical slot 125 in tube 96 wherein it is operatively connected to the rod 94. As seen in FIG. 7, the lower end 126 of rod 94 is connected through a conventional rotatable coupling 128 to a yoke 130. The latter is pivotally connected through a pin 132 to a link 134 which is pivotally connected by a pin 136 to the end 124 of lever 114. Yoke 130 and pin 132 form a universal joint connection rod 94 and lever 114, while the rotatable coupling 128 permits relative rotation of rod 94 about its vertical axis, with respect to the yoke.

A slide block 138 is secured to the lower end of rod 94 to guide vertical sliding movement of the rod in tube 96. A spring 140 engaged between the lower end of slide block 138 and the upper end of yoke 130 stabilizes the yoke in its vertical position. With this arrangement, it will be seen that rotation of cam 110 by motor 88 will cause arm 114 to oscillate between the extreme upper and lower positions shown in FIG. 7. This will cause sampling tube 22 to move between its upper and lower positions.

When the circuit between light emitting diode 84 and the photo-transistor 86 is broken, motor 88 is actuated to commence rotation of the cam 110 from the position shown in solid lines in FIG. 7, towards the phantom line positions thereof. This lowers sampling tube 22 into the sample container at the sampling station 20, permitting tube 22 to aspirate a sample of the liquid in the container. Continued operation of motor 88 continues rotation of cam 110 and this eventually moves lever 114 towards its upper position, raising the sampling tube out of the sampling container. When the sampling tube moves out of the liquid in the container, air is aspirated into the tube and serves as a buffer separating that sample from the next sample to be taken.

When sampling tube 22 reaches its upper dotted line position shown in FIG. 3, the tube is swung horizontally from the sampling station to a position over the wash liquid receptacle 23. The mechanism for causing this horizontal swinging movement of the sampling tube is shown in detail in FIGS. 6, 7 and 9. As seen therein, the upper end 150 of tube 96 rotatably receives a bushing 152, while its lower end 154, rotatably receives a support bearing 156, so that tube 96 can rotate about its vertical axis. Bushing 152 includes internal bearings 158 that surround rod 94 to permit it to rotate with respect to the bushing.

Figure 9:
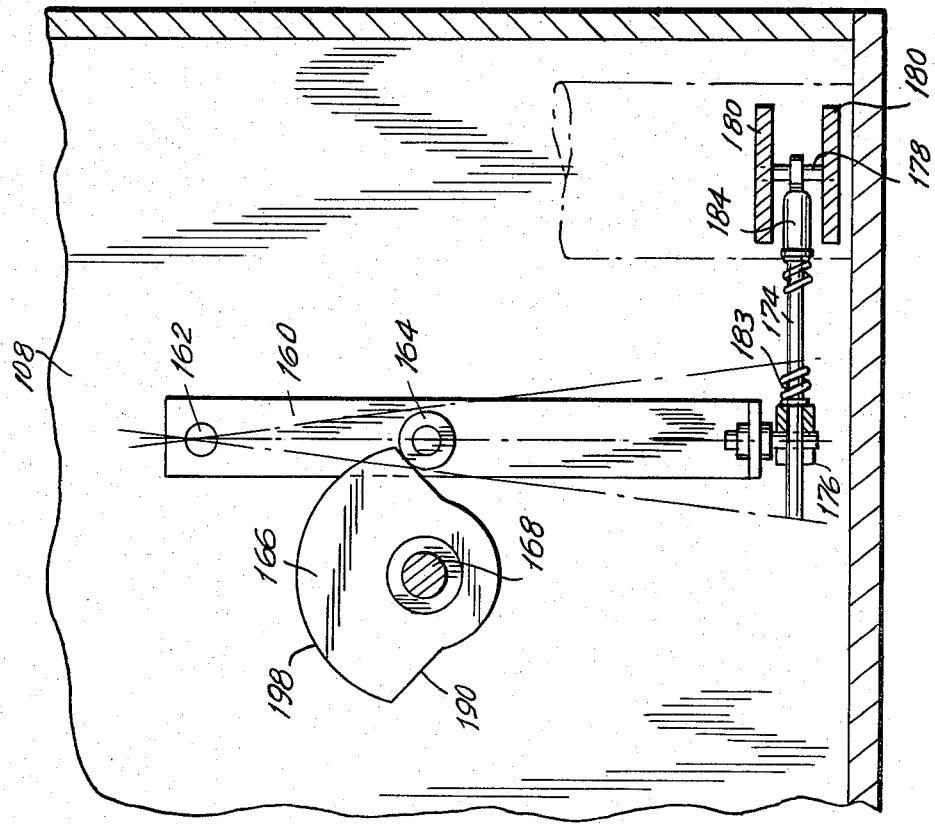
FIG. 9 is a sectional view of the drive mechanism for oscillating the sampling tube from its position over the sample container to its position over the wash liquid receptacle, taken along line 9—9 of FIG. 6.

Rotation of tube 96 is accomplished by the cam and lever arrangement shown in FIG. 9. As seen therein, a lever 160 is pivotally mounted at 162 on the sidewall of subhousing 108. This lever carries a cam follower 164 intermediate its ends which engages a cam 166. The latter is secured to a shaft 168 which is rotatably mounted in subhousing 108. A gear 170 is also secured to shaft 168 for rotation therewith, and is drivingly engaged with a gear 172 secured to shaft 104. Thus, operation of motor 88 drives gears 170, 172 to cause rotation of cam 166. This gearing arrangement is selected such that cam 110 rotates through 360° under the drive of shaft 104, while cam 166, during the same time period, rotates only through 180°.

The lower end of lever 160 is pivotally engaged with a link 174 through a connecting block 176. The opposite end of link 174 is pivotally connected at 178 to a pair of projecting crank ears 180 rigidly secured to tube 96. A coil spring 183 extending between link 174 and subhousing 108 urges lever 160 to the left in FIG. 9 and maintains engagement of cam follower 164 against cam 166. Rotation of cam 166, particularly along the inclined surfaces 190 thereof, will cause oscillation of tube 96 about its vertical axis.

Rod 94 is keyed to the tube 96 for rotation therewith by a transverse pin 192 which extends through the slide-block 138 into a pair of opposed vertical slots 194 formed in the tube. These slots permit rod 94 to move vertically, while the engagement of pin 192 in the slots insures that rod 94 will oscillate with tube 96. Such oscillation moves sampling tube 22 between sampling station 20 and its position over the wash liquid receptacle 23, as previously described.

Cam 166 is arranged relative to cam 110 such that arcuate swinging movement of the sampling tube 22 from the sampling station commences when the sampling tube 22 reaches the upper most phantom line position in FIG. 3. The tube remains in this upper position under the influence of cam 110, as it moves to the position over the wash liquid receptacle, and remains generally in that upper position under the influence of cam 110 while it is immersed in the wash liquid. When the sampling tube arrives at its position over the wash liquid receptacle, cam follower 164 engages the long, larger diameter sector 198 of cam 166 and the sampling tube thus remains in this position during that portion of the rotation of cam 166.

Figure 8:
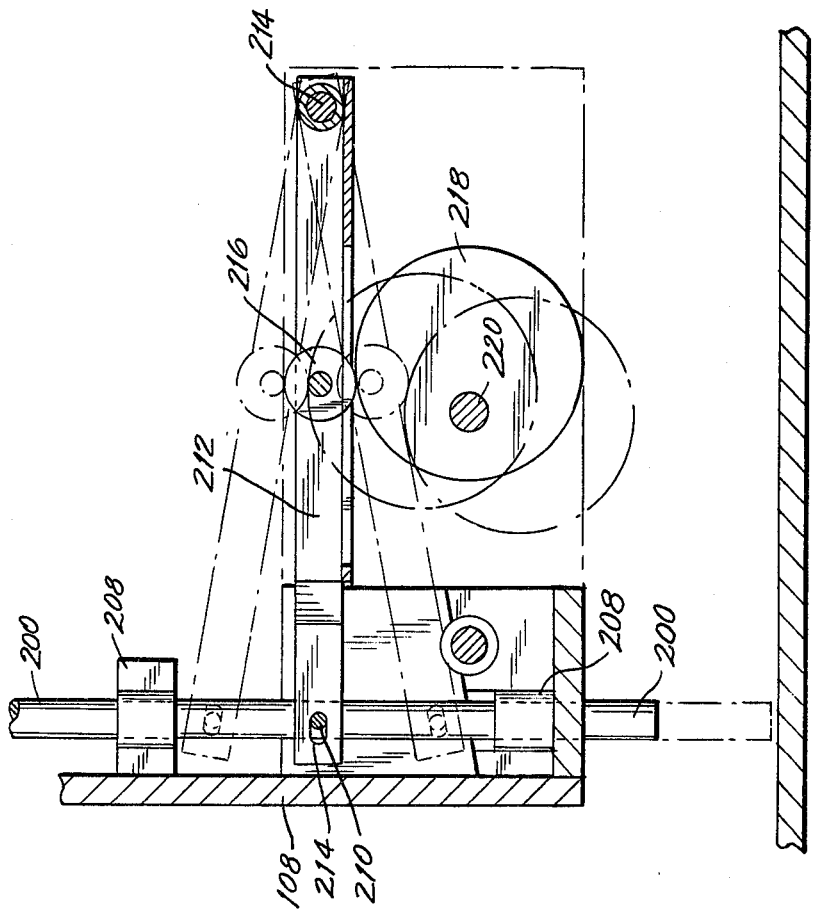
FIG. 8 is a sectional view of the drive mechanism for raising and lowering the wash liquid receptacle, taken along line 8—8 of FIG. 6.
Figure 10:
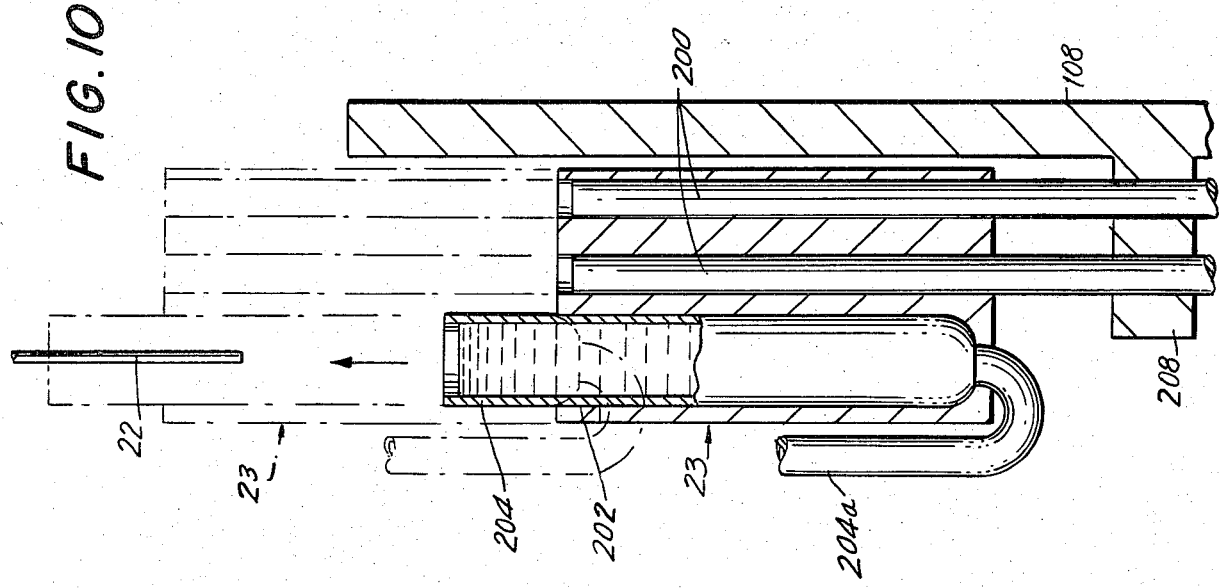
FIG. 10 is a sectional view taken along line 10—10 of FIG. 1 showing the vertical reciprocation of the wash liquid receptacle.

When sampling tube 22 is in position over the wash liquid receptacle, that receptacle is raised to immerse the sampling tube in the wash liquid, in order to cleanse the tube and permit aspiration of a portion of the wash liquid into the tube so that the interior thereof is also cleansed. Vertical movement of the wash liquid receptacle is also under the control of motor 88 and the cam arrangement associated therewith, shown in detail in FIGS. 6, 8 and 10. As seen therein, the receptacle has a pair of enlarged openings 202 formed therein that receive liquid receptacles 204, such as for example, test tubes. These receptacles are open at their bottom and communicate with a liquid supply port 204. A discharge tube 206 also communicates with the container 204, so that a continuous flow of wash liquid through the container is provided in any convenient manner in order to avoid contamination of the sampling tube.

Receptacle 23 is rigidly secured to a pair or rods 200 which are slidable mounted in fixed brackets 208, in subhousing 108. These rods are each connected through a pin 210 to a lever 212. The latter has an elongated lost-motion slot 214 formed therein which receives pin 210 to permit arcuate movement of the lever and vertical reciprocation of the rods 200.

Lever 212 is pivotally mounted at 214 in subhousing 108 and carries a rotatable cam follower 216 intermediate its ends. This cam follower engages a circular cam 218 secured to a drive shaft 220. The weight of the wash liquid receptacle on the arm 212 maintains engagement between cam follower 216 and cam 218.

Shaft 220 is rotatably received in sleeve bearings 222 in subhousing 108, and its free end 224 is drivingly engaged with a gear 226. The latter engages gear 102, and thus is driven by motor 88.

Cam 218 is arranged with respect to cam follower 216 such that upward movement of wash liquid receptacle 23 commences when sampling tube 22 arrives at its position above the receptacle. Upward movement of the receptacle, as indicated in phantom lines in FIG. 10, immerses the tube in the wash liquid. The movement of the wash liquid receptacle is a continuous motion and as soon as it arrives at its upper position it begins to retract downwardly. By the time the receptacle has moved downwardly a distance sufficient to clear the ends of sampling tube 22, cam 166 has reached the end of the sector portion 198 thereof, so that its cam follower now moves down the sloped surface 190, to cause tube 96 to rotate in a counterclockwise direction, as seen in FIG. 1, returning the sampling tube to its position at sampling station 20. At the same time, sampling tube 22 is held in its upper position by cam 110. When the sampling tube arrives at the sampling station, motor 88 is automatically turned off, by an automatic timing circuit in the controls of the apparatus. The timing circuit is of conventional construction, and need not be described herein in detail.

Upon movement of the sampling tube from the sampling station to the wash liquid receptacle, the control circuit of the apparatus operates motor 66 to drive carrier disk 62 and move the next sampling container into position at the sampling station. The drive to the motor 66 is terminated when the circuit between light emitting diode 84 and photo-transistor 86 is broken by the movement of a sampling container therebetween. However, the controls of the apparatus include a separate timing circuit so that if, after a predetermined time of operation of motor 66, no sampling container breaks the circuit between elements 84, 86, the supply of power to motor 66 is cut off. Thus, by simply eliminating a sampling container from the series of openings in the carrier disk after the last sample to be tested, the operator can insure automatic shut off of the device. If desired, the control circuit may include a control signal apparatus which will operate motor 66 after the last sample in reverse, to return the device to its starting position.

Accordingly, it is seen that a relatively simply constructed liquid sampling apparatus is provided which enables a large quantity of samples to be moved into position at a sampling station and automatically sampled. In addition, the apparatus provides for a simple and convenient method of cleansing the sampling tube after each sampling operation.

Although an illustrative embodiment of the present invention has been described herein with reference to the accompanying drawings, it is to be understood that the invention is not limited to that precise embodiment, and that various changes and modifications may be effected therein by one skilled in the art without departing from the scope or spirit of this invention.

What is claimed is:

1. Liquid sampling apparatus comprising a sample carrier mounted in the apparatus for carrying a plurality of sample containers thereon on which to maximize the number of sample containers which may be carried the containers are arrayed in a generally spiral pattern, a sampling station in the apparatus, means for successively moving said sample carrier rotationally and laterally such that said sample containers are successively moved into said sampling station, a receptacle for containing a wash liquid located spaced from said sampling station, and means for removing a sample of liquid from each sample container, in turn, at said sampling station including a sampling tube and means for moving said sampling tube from said sampling station to and into said receptacle and returning said sampling tube to the next successive sample container at said sampling station, with said sample carrier being moved laterally and rotationally between successive positionings of said sampling tube at said sampling station so that each of said sample containers is placed at said sampling station to permit automatic sampling of the contents thereof.

2. Liquid sampling apparatus comprising a support arm pivotally mounted in said apparatus, a sample carrier disk rotatably mounted by a pivot mounting thereof on said support arm for carrying a plurality of sample containers thereon arrayed in a generally spiral pattern about the pivot mounting of said disk with said spiral array pattern extending from a radial outer position to a radial inner position with respect to said pivot mounting, a sampling station in said apparatus, means for successively moving said sample containers into said sampling station by rotating said disk and pivoting said support arm thereby to successively position said spirally arrayed containers at said station; a wash liquid receptacle disposed spaced from said sampling station for containing a wash liquid, and means for removing a sample of liquid from a sample container at said sampling station including a sampling tube and means for moving said sampling tube from said sampling station to and into said receptacle and then back again to said sampling station, said sampling means permitting sampling of each said sample container, in turn, at said sampling station, without sample containers at the radial outer position interfering with sampling any other sample containers at lesser radial positions.

3. Liquid sampling apparatus comprising a sampling station, a support arm pivotally mounted in said apparatus, a sample carrier disk rotatably mounted by a pivot mounting thereof on said support arm for carrying a plurality of sample containers thereon in which, to maximize the number of such sample containers carried on said disk, the containers are arrayed in a generally spiral pattern about the pivot mounting of said disk, said spiral pattern being disposed such that when said sample carrier disk is moved laterally and rotationally the sample containers thereon pass through said sampling station, means intermittently sampling the contents of said containers, in turn, when the same are disposed at said sampling station, a cam disk rotatably mounted on said support arm in spaced relation to said carrier disk and operatively engaged with said carrier disk for rotation therewith; said cam disk having a generally spiral-shaped cam slot formed therein which is generally complementary to the spiral array of said containers, a cam follower engaged in said slot and located in a fixed position in said apparatus, and means for intermittently rotating said disks on said arm so that the arm is pivoted as a result of the engagement of said cam disk slot with said cam follower as the carrier disk is rotated, thereby to successively move said containers through said sampling station.

4. Liquid sampling apparatus as defined in claim 3 including a wash liquid receptacle disposed at a location spaced from said sampling station for containing a wash liquid and means disposed at said sampling station at least during a sampling operation for removing a sample of liquid from a sample container at said station including a sampling tube and means for moving said sampling tube from said sampling station to and into said receptacle and then back to said sampling station.

5. Liquid sampling apparatus comprising a sample carrier mounted in said apparatus for carrying a plurality of sample containers, a sampling station in said apparatus, means for successively moving said sample containers into said sampling station, a wash liquid receptacle disposed at a location spaced from said sampling station for containing a wash liquid, means for removing a sample of liquid from a sample container at said sampling station including a sampling tube and means for moving said sampling tube from said sampling station to a position above said receptacle and back again, and means for selectively raising said receptacle to immerse the tube in the liquid in the receptacle to wash the sampling tube when the same is at its position above the receptacle and for thereafter lowering the receptacle before the tube is returned to said sampling station.

6. Liquid sampling apparatus comprising a sample carrier movably mounted in said apparatus for carrying a plurality of sample containers thereon, a sampling station in said apparatus, means for successively moving said sample containers into said sampling station, a receptacle for containing a wash liquid movably mounted for vertical movement in said apparatus at a location spaced from said sampling station, and means for removing a sample of liquid from a sample container at said sampling station including a sampling tube, means for supporting said sampling tube adjacent said sampling station for both vertical and horizontal pivotal movement, means for moving said sampling tube vertically with respect to said sampling station between a lowered position wherein the tube is inserted into a sample container at said station and a raised position above the sampling station, means for pivoting said tube from said raised position over the sampling station to a position over said receptacle, and means for moving said receptacle between a first, lowered position and a second, raised position, such that when said tube is pivoted to its position over said receptacle, the receptacle is moved to its raised position and the tube is immersed in the wash liquid contained in the receptacle following which the receptacle is moved to its lowered position so that the sampling tube can again be moved to its position above the sampling station.

7. Liquid sampling apparatus comprising a support arm pivotally mounted in said apparatus, a sample carrier disk rotatably mounted on said support arm for carrying a plurality of sample containers thereon arrayed in a generally spiral pattern about the pivot mounting of said disk, a sampling station in said apparatus, means for successively moving said sample containers into said sampling station by simultaneeously rotating said disk and pivoting said support arm thereby to successively position said spirally arrayed containers at said station; a receptacle for containing a wash liquid located adjacent said sampling station, and means for removing a sample of liquid from a sample container at said sampling station including a sampling tube and means for moving said sampling tube from said sampling station to a position above said receptacle and back again, and means for selectively raising said receptacle to immerse the tube in the liquid in the receptacle to wash the tube and for thereafter lowering the receptacle before the tube is returned to said sampling station.

8. Liquid sampling apparatus comprising a sampling station, a support arm pivotally mounted in said apparatus, a sample carrier disk rotatably mounted on said support arm for carrying a plurality of sample containers thereon arrayed in a generally spiral pattern about the pivot mounting of said disk, said spiral pattern being located on said disk to pass through said sampling station when rotation of the disk is coordinated with oscillation of said arm; a cam disk rotatably mounted on said support arm in spaced parallel relation to said carrier disk and operatively engaged with said carrier disk for simultaneous rotation therewith; said cam disk having a generally spirally shaped cam slot formed therein which is generally complementary to the spiral array of said containers; a cam follower engaged in said slot and located in a fixed position in said apparatus; means for intermittently rotating said disks on said arm whereby the arm is pivoted upon rotation of the disk as a result of engagement of said cam disk slot and follower thereby to successively move said containers through said sampling station; a receptacle for containing a wash liquid movably mounted in said apparatus for vertical movement between upper and lower positions adjacent said sampling station; and means for removing a sample of liquid from a sample container at said sampling station including a sampling tube, means for mounting said sampling tube adjacent said sampling station for both vertical and horizontal pivotal movement; means for moving said sampling tube vertically with respect to said sampling station between a lower position wherein the tube is inserted in a sample container at said station and a raised position above the sampling station, and means for pivoting said tube from said raised position over the sampling station to a position over said receptacle; and means for moving said receptacle between its lower position and its upper position when the tube is positioned over the receptacle to immerse said tube in the liquid contained in said receptacle.

9. Liquid sampling apparatus as defined in claim 8 wherein said means for moving and pivoting said sample tubes and for moving said receptacle respectively, include a pivotally mounted lever and a cam for oscillating the associated lever, said cams being positioned relative to each other to move said tube and receptacle in a predetermined sequential pattern after a container enters said sampling station; and an electric motor for driving said cams.

10. Liquid sampling apparatus as defined in claim 9 including means for activating said electric motor when a container enters said sampling station.

11. Liquid sampling apparatus as defined in claim 9, wherein said carrier disk has a plurality of openings formed therein in said spiral array and means removably mounted in said openings for supporting said containers.

12. Liquid sampling apparatus as defined in claim 5 wherein said means for moving said sampling tube dips said sampling tube into the sampling container at the sampling station for removing said sample therefrom, then lifts said sampling tube to an elevated position out of said sampling container, but maintains said sampling tube at its elevated position when said sampling tube is in the position over said receptacle.

13. Automatic liquid sampling apparatus in which a plurality of sample containers are arranged on a sample carrier such that an increased number of said sample containers can be accomodated on said carrier without an increase in overall size of the apparatus, comprising a housing, a sample carrier disk carrying said plurality of sample containers thereon in a continuous spiral array coiling from an outermost position near a rim of said disk to an innermost position near a center of said disk; a shaft mounting said disk at its center; a support sleeve supporting said shaft and permitting rotation thereof; a cam disk having a spiral camway thereon and affixed at its center to said shaft so as to be coaxial with said sample carrier disk, the spiral camway being complementary to the spiral array of said sample containers on said sample carrier disk; a support arm movably mounted in said apparatus supporting said support sleeve for permitting horizontal and rotational movement of said sample carrier disk and said cam disk; a cam follower fixedly mounted in said apparatus in engagement with said spiral camway; sampling means including a sampling tube and sampling tube support means moving said sampling tube horizontally to a predetermined sampling station in said apparatus and bringing said sampling tube into a sample container at such station to remove a sample of liquid therefrom; means for detecting the presence of a sample carrier at said sampling station; and drive means for moving said sample carrier disk after a sample of liquid has been withdrawn from one sample carrier at said sampling station so that said carrier disk moves horizontally and rotationally, under the guidance of said engaged camway and cam follower, until a subsequent sample container is detected to be present at said sampling station.

14. Automatic liquid sampling apparatus according to claim 13, further comprising a wash receptacle disposed at a predetermined position spaced from said sampling station, and said sampling tube support means operates to move said sampling tube horizontally to said predetermined position after said liquid is withdrawn from said one sample container and includes means for immersing said tube in said wash receptacle before returning said tube to said sampling station.

* * * * *